United States Patent
Bayer et al.

(10) Patent No.: US 8,110,088 B2
(45) Date of Patent: Feb. 7, 2012

(54) IMPLANT AND METHOD FOR MANUFACTURING SAME

(75) Inventors: Ullrich Bayer, Admannshagen-Bargeshagen (DE); Baerbel Becher, Rostock (DE); Bernd Block, Rostock (DE); Robert Voegele, Rostock (DE); Patricia Decker, Schwaan (DE)

(73) Assignee: BIOTRONIK VI Patent AG, Baar (CH)

( * ) Notice: Subject to any disclaimer, the term of this patent is extended or adjusted under 35 U.S.C. 154(b) by 53 days.

(21) Appl. No.: 12/564,342

(22) Filed: Sep. 22, 2009

(65) Prior Publication Data
US 2010/0087915 A1    Apr. 8, 2010

(30) Foreign Application Priority Data

Oct. 6, 2008 (DE) .......................... 10 2008 042 602
Apr. 29, 2009 (DE) .......................... 10 2009 002 709

(51) Int. Cl.
*C25F 1/00*    (2006.01)

(52) U.S. Cl. .......................................... 205/640; 148/95
(58) Field of Classification Search ................. 205/640; 148/95
See application file for complete search history.

(56) References Cited

U.S. PATENT DOCUMENTS

| | | | | |
|---|---|---|---|---|
| 3,817,849 A | * | 6/1974 | Blosser et al. | 204/157.44 |
| 4,704,126 A | * | 11/1987 | Baswell et al. | 623/10 |
| 6,679,980 B1 | * | 1/2004 | Andreacchi | 204/272 |
| 2009/0050334 A1 | * | 2/2009 | Marya et al. | 166/376 |

* cited by examiner

*Primary Examiner* — Alexa D. Neckel
*Assistant Examiner* — Nicholas A. Smith
(74) *Attorney, Agent, or Firm* — Biotech Beach Law Group PC

(57) ABSTRACT

The present invention relates to a method for manufacturing an implant, in particular an intraluminal endoprosthesis, with a body containing metallic material, preferably iron. To control the degradation of the implant, the method comprises the following steps: a) preparing the body of the implant, and b) incorporating hydrogen into at least a portion of the structure of the implant body near the surface. Furthermore, such an implant is described.

6 Claims, No Drawings

IMPLANT AND METHOD FOR MANUFACTURING SAME

CROSS REFERENCE TO RELATED APPLICATIONS

The present invention claims benefit of priority to Germany patent application number DE 10 2008 042 602.4, filed on Oct. 6, 2008 and Germany patent application number DE 10 2009 002 709.2, filed on Apr. 29, 2009; the contents of each are herein incorporated by reference in their entirety.

FIELD OF THE INVENTION

The present invention relates to a method for manufacturing an implant, in particular an intraluminal endoprosthesis.

BACKGROUND OF THE INVENTION

Medical endoprostheses or implants for a wide variety of applications are known in large numbers from the prior art. Implants in the sense of the present invention are understood to be endovascular prostheses or other endoprostheses, e.g., stents, fastening elements for bones, e.g., screws, plates or nails, surgical suture materials, intestinal clamps, vascular clips, prostheses in the area of hard and soft tissue as well as anchoring elements for electrodes, in particular pacemakers or defibrillators.

Stents are used as implants especially frequently today for treatment of stenoses (vascular occlusions). They have a body in the form of a tubular, possibly perforated, or hollow cylindrical basic mesh, which is open at both longitudinal ends. The tubular basic mesh of such an endoprosthesis is inserted into the blood vessel to be treated and serves to support the blood vessel. Stents have become established for treatment of vascular diseases in particular. Through the use of stents, constricted areas in the vessels can be dilated, resulting in a wider lumen. Although an optimum vascular cross section, which is needed primarily for successful treatment, can be achieved by using stents or other implants, the permanent presence of such a foreign body initiates a cascade of microbiological processes, leading to a gradual overgrowth of the stent and in the worst case to a vascular occlusion. One approach to solving this problem consists of manufacturing the stent and/or other implants from a biodegradable material.

The term "biodegradation" is understood to refer to hydrolytic, enzymatic and other metabolic degradation processes in a living organism, where these processes are caused mainly by the body fluids coming in contact with the biodegradable material of the implant and leading to a to gradual dissolution of the structures of the implant containing the biodegradable material. The implant loses its mechanical integrity at a certain point in time through this process. The term "biocorrosion" is often used as synonymous with the term "biodegradation." The terms "bioresorption" and "bioabsorption" refer to the subsequent resorption or absorption of the degradation products by the living organism.

Materials suitable for implants that are biodegradable in the body may contain polymers or metals, for example. The implant body may be made of several of these materials. These materials have in common their biodegradability. Examples of suitable polymer compounds are the polymers from the group comprising cellulose, collagen, albumin, casein, polysaccharides (PSAC), polylactide (PLA), poly-L-lactide (PLLA), polyglycol (PGA), poly-D,L-lactide-co-glycolide (PDLLA-PGA), polyhydroxybutyric acid (PHB), polyhydroxyvaleric acid (PHV), polyalkyl carbonates, polyorthoesters, polyethylene terephtalate (PET), polymalonic acid (PML), polyanhydrides, polyphosphazenes, polyamino acids and their copolymers as well as hyaluronic acid. Depending on the desired properties, the polymers may be present in pure form, in derivatized form, in the form of blends or as copolymers. Biodegradable metallic materials are based on alloys of magnesium and/or iron. The present invention preferably relates to implants whose biodegradable material contains at least partially a metal, preferably iron, manganese, zinc and/or tungsten, in particular an iron-based alloy (hereinafter simply "iron alloy").

One goal in the implementation of biodegradable implants is to control degradability in accordance with the desired treatment and/or use of the respective implant (coronary, intracranial, renal, etc.). For many therapeutic applications, for example, an important target corridor is that the implant must lose its integrity after a period of four weeks to six months. The term "integrity." i.e., mechanical integrity, is understood to refer to the property whereby the implant has hardly any mechanical losses in comparison with the undegraded implant. This means that the implant still has so much mechanical stability that the collapse pressure, for example, has declined only slightly, i.e., to 80% of the nominal value at most. The implant may thus retain its main function, namely keeping the blood vessel open, while retaining its integrity. Alternatively, integrity may be defined as meaning that the implant still has so much mechanical stability that it is hardly subject to any geometric changes in its stress state in the vessel; for example, it does not collapse to any significant extent, i.e., it still has 80% of the dilatation diameter under stress or, in the case of a stent, hardly any of the load-bearing struts are broken.

Implants with am iron alloy, in particular stents containing iron, are especially inexpensive and simple to manufacture. For treatment of stenoses, for example, these implants lose their mechanical integrity and/or supporting effect only after a comparatively long period of time, i.e., only after remaining in the treated body for approx. two years. This means that in this application, the collapse pressure of implants containing iron declines too slowly over a period of time.

Various mechanisms of controlling the degradation of magnesium implants have already been described in the prior art. For example, these are based on organic and inorganic protective layers or combinations thereof which present a resistance to the human corrosion medium and the corrosion processes taking place there. Approaches known in the past for solving this problem have been characterized in that barrier layer effects are achieved, based on a spatial separation, preferably free of defects, between the corrosion medium and the metallic material. These approaches result in a longer degradation time. Thus, the degradation protection is ensured by variously formulated protective layers and by defined geometric distances (diffusion barriers) between the corrosion medium and the degradable base material of the implant body (e.g., magnesium or Mg alloys). Other approaches are based on alloy components of the biodegradable material of the implant body, which influence the corrosion process by displacement of the position in the electrochemical voltage series. Other approaches in the field of controlled degradation induce intended breaking effects by applying physical changes (e.g., local changes in cross section) and/or chemical changes in the stent surface (e.g., multilayers with different chemical compositions locally). However, with the approaches mentioned so far, it is not usually possible to make the dissolution due to the degradation process and its resulting breakage of webs occur in the required time window. The result is that degradation of the implant begins either too early or too late or there is too much variability in the degradation.

SUMMARY OF THE INVENTION

Consequently, a feature of the present invention is to provide a method for manufacturing an implant, which will allow degradation of the implant in the desired target corridor, especially in the case of implants with an iron-based alloy in a shorter interval of time. The degradation should take place at a controllable point in time. Accordingly, the object of the invention is also to create such an implant.

The above feature is achieved by a method comprising the following steps:
a) preparing the body of the implant.
b) incorporating hydrogen into at least a portion of the structure of the implant body near the surface.

In another aspect of the present invention an intraluminal endoprosthesis implant with a body including a metallic material, optionally iron, is provided by the methods described herein.

DETAILED DESCRIPTION OF THE INVENTION

In the present invention, the body of the implant comprises at least a portion of the implant, preferably the main portion of the implant which achieves the mechanical integrity of the implant.

The term "structure" as used below is understood to refer to the arrangement of the components of solids (solid states), in particular the arrangement of crystallites (grains), pores, amorphous regions and grain boundary regions of the implant body. Furthermore, the term "structure near the surface" is understood to refer to the volume range of the structure of the implant body extending from the surface down to a certain (slight) depth of the implant body. This volume range of the implant body extending from the surface down to a certain (slight) depth is also referred to as the "boundary layer of the implant body near the surface" or simply as "boundary layer."

The advantage of the inventive method is that through the incorporation of hydrogen, preferably atomic hydrogen, embrittlement of the structure occurs, and is manifested in an increase in the strength of the structure near the surface and an associated worsening of the strain properties of this area of the structure. In this way, depending on the average grain size of the implant body material in the present case, local damage is induced in the material in the area of the implant body near the surface. The embrittling effect of hydrogen causes degradation to be accelerated in this region due to the accelerated dissolution of crystallites out of the composite structure in particular. The accelerated dissolution of crystallites is achieved in particular because the highest hydrogen concentration usually occurs at the grain boundaries. The grains dissolved out are removed from the surface of the implant through the surrounding body fluid as well as preferably corroding or dissolving. The remaining surface of the implant is roughened due by dissolving out the crystallites and/or being provided with a fissured structure. Subsequently there is an increased surface area, which contributes toward even more accelerated degradation of the implant.

Since the boundary layer enriched with hydrogen has a higher defect density than the structural areas underneath that, the structural areas near the surface have a lower elongation at break. Cracks occurring due to the higher defect density run from the boundary zone in the direction of the implant body that is not loaded with hydrogen, where they are stopped by the high crack-energy-absorbing capacity of the base material.

In a preferred exemplary embodiment, hydrogen is incorporated into the structure of a boundary layer arranged near the surface of the implant body, whereby the boundary layer has to a thickness of max. 15 µm.

The boundary layer arranged near the surface, having an increased concentration of hydrogen, must extend starting from the surface to an optimum depth, which is indicated for the respective application because there is the risk that in hydrogen loading over an excessive volume area, the implant may break due to delayed brittle fracture during or after a mechanical stress, e.g., in dilatation of the stent. The depth of loading is determined by the degree of deformation of the metal material, preferably the iron alloy, the recrystallization state and the resulting average particle size produced, the method by means of which the hydrogen is incorporated, the composition of the reagents involved as well as the composition of the volume of the implant body near the surface.

In another preferred exemplary embodiment, the average concentration of hydrogen in the structural areas of the implant body where the incorporation of hydrogen takes place is approx. 50 ppm to approx. 150 ppm after the conclusion of the incorporation. For comparison: the structural areas of the implant which are not additionally loaded with hydrogen have a max. hydrogen content of 15 ppm.

A hydrogen concentration within the stated concentration range in the respective structural areas near the surface has the result that, first, the hydrogen concentration is not selected to be too high; the surface areas are not dissolved immediately and directly from the implant, and furthermore, the degradation is accelerated. However, accelerated degradation may also be achieved even at low hydrogen concentration levels, e.g., in the range of 30 ppm, when the part of the implant body treated has an increased degree of deformation.

An especially simple and inexpensive method of achieving an incorporation of hydrogen in a portion of the structure of the implant body near the surface consists of pickling at least a portion of the implant body by means of an inorganic acid and then rinsing it in distilled water. The acids HCl and/or $HNO_3$ are especially preferably used for pickling. A subsequent rinsing in distilled water causes the pickling process to stop and thus stops further hydrogen incorporation into the structure of the implant body.

Furthermore, the structure of the body surface which has been roughened due to the pickling may also serve as a substance reservoir for another coating, which is to be described in greater detail below by means of an active pharmaceutical substance, which is incorporated in the form of nanoparticles or microparticles and may comprise, for example, substances to promote bone growth, such as calcium phosphates, temporary contrast agents and/or cell-growth-inhibiting substances and/or radioactive substances. Furthermore, lubricants may be effectively incorporated into the roughened structure to reduce the coefficient friction in a catheter.

Essential process parameters of the pickling process by means of which the degradation properties can be adjusted include the pickling medium composition, the pickling temperature and the pickling time. Furthermore, material parameters of the implant body also play a role, in particular the composition of the material, the deformation state, the grain size and the composition of the material at the surface and/or in the immediate vicinity of the surface.

In another exemplary embodiment, as an alternative to pickling or after the pickling step, at least a portion of the implant body is immersed in an acidic to basic electrolyte system for the incorporation of hydrogen, and then is connected to the cathode of a voltage source, which is preferably acted upon with a current density approx. 0.5 A/dm$^2$ to approx. 2 A/dm$^2$. The implant body is therefore electrically connected to connecting wires containing titanium, for example. A counter-electrode made of acid-resistant stainless steel is situated in the electrolyte container.

After immersing the implant in the electrolyte, the implant is connected to the cathode and the specified current density is applied. The effects taking place at the interface between the aqueous electrolyte and the implant surface result in an increased dissociation of the aqueous electrolyte, which is associated with an increased evolution of hydrogen. Because of the cathodic connection, a large portion of the hydrogen begins to diffuse into the implant. Depending on the diffusion flow of hydrogen in the implant body material, which is adjustable through the process parameters, depending on the applied potential, the treatment time and the structural status of the material of the implant body, which results from the deformation of the alloy, for example, the grain size and the composition of the material at the surface and/or in the immediate vicinity of the surface, this results in an incorporation of hydrogen into the structural areas of the implant body near the surface, which proceeds differently with regard to the rate and depth of penetration and determines the duration of the degradation achieved. In addition, this incorporation also depends on the lattice structure of the material of the implant body. For example, the hydrogen diffusion coefficient in an iron alloy containing 20 wt % Mn with a face-centered cubic lattice is lower than that with the body-centered cubic lattice of pure iron. The grain boundaries in particular serve as thermodynamically preferred diffusion pathways of hydrogen. The degradation properties of the treated implant also depend on the composition of the galvanic electrolyte and the electric parameters. Hydrogen loading of the implant body is also accompanied by a roughening of the surface of the implant.

Another advantage of the inventive method according to the above exemplary embodiment is that the cathodically-supported surface treatment requires a plant technology that is not very cost-intensive. The surface treatment may be conducted in galvanic installations for the deposition of gold. For the cathodically-supported surface treatment, such an installation need only have an acid-resistant container and counter-electrodes of chemically-resistant materials, e.g., a perforated plate of platinum-plated titanium.

The aqueous electrolyte system preferably has contains between 20 and 30 vol % of an 85% phosphoric acid.

In another preferred exemplary embodiment, the electrolyte system into which the implant body is dipped contains at least one phosphate. In particular when the implant surface contains iron, the surface of the implant body becomes enriched with biocompatible iron phosphate compounds due to the presence of phosphate in the electrolyte. Since the biocompatible iron phosphate compounds are deposited on the surface and incorporated into areas of the implant near the surface, irritation of cells is reduced or prevented. Direct contact between the material of the implant body, preferably containing iron, and the surrounding cellular tissue is thus postponed until a time which is farther from the point in time than is the case with traditional implants.

Another advantage is that after the hydrogen has been incorporated, the implant body is coated with magnesium stearate and/or parylene and/or an active pharmaceutical substance over at least a portion of its surface, the active pharmaceutical substance in particular being embedded in a polymer, e.g., a polylactide, a polyglycoside or a copolymer thereof, especially preferably PLLA or PLGA or a blend of the aforementioned polymers.

The phrase "active pharmaceutical substance" (or active therapeutic substance or therapeutically active substance) in the sense of the present invention is understood to be a plant-based, animal-based or synthetic active ingredient, i.e., a drug (medication) or hormone used in a suitable dosage as a therapeutic agent for influencing states or functions of the body, as a replacement for active ingredients synthesized by the human or animal body, e.g. insulin, and to eliminate disease pathogens, tumors, cancer cells or exogenous substances or to render them harmless. The release of the substance in the environment of the implant has a positive effect on the course of healing or counteracts pathological changes in the tissue as a result of the surgical procedure and in oncology serves to render malignant cells harmless.

Such active pharmaceutical substances have an anti-inflammatory and/or antiproliferative and/or spasmolytic effect, for example, so that restenoses, inflammations or (vascular) spasms, for example, can be prevented. Such substances may include, for example, one or more substances from the group of active agents such as calcium channel blockers, lipid regulators (e.g., fibrates), immunosuppressants, calcineurin inhibitors (e.g. tacrolimus), antiphlogistics (e.g., cortisone or diclofenac), anti-inflammatories (e.g. imidazoles), antiallergics, oligonucleotides (e.g. dODN), estrogens (e.g., genistein), endothelializing agents (e.g., fibrin), steroids, proteins, hormones, insulins, cytostatics, peptides, vasodilators (e.g., sartans) and substances having an antiproliferative effect, namely taxols or taxans, preferably paclitaxel or sirolimus here.

A coating by means of a polymer, e.g., a polylactide, a polyglycoside or a copolymer thereof, especially preferably PLLA or PLGA or a blend of the aforementioned polymers containing the active pharmaceutical substance is especially advantageous because the reduction in pH achieved in degradation of the polymer in the area of the implant surface constitutes an additional acceleration factor for corrosion, in particular in the case of an implant with an iron alloy.

Coating of the surface of the implant with parylene and/or magnesium stearate after incorporation of hydrogen is advantageous because the surface properties of the implant are to a certain extent "frozen" in this form after incorporation of hydrogen due to the coating above it. In this way, the surface properties, which would otherwise depend on the duration of storage or shipping of the implant until it is introduced into the body to be treated and thus also the degradation, time can be adjusted reproducibly and in a defined manner.

The great ability of parylene to penetrate into gaps has an advantageous effect, so there is deep penetration of parylene into rough surfaces created by the hydrogen treatment, down to the base of the gaps. The permeation properties for water, chloride solutions and hydrogen that are characteristic of parylene ensure an especially well-controlled degradation behavior of the implant in combination with the underlying hydrogen-loaded boundary layer near the surface.

This is characterized by a uniform slow corrosion process over the cross section of the implant.

Parylene is a completely linear, partially crystalline, uncrosslinked aromatic polymer. The various polymers have different properties and can be divided into four basic types, namely parylene C, parylene D, parylene H and parylene F. Parylene C is preferred for use as an additional coating after hydrogen loading.

By means of the inventive method, in coating with magnesium stearate, an implant characterized by a defect-free body surface due to subsequent sealing can be manufactured. Local defects and/or pores present on the surface of the implant body and roughened areas are effectively protected from contact with body fluids having a corrosive action. The hydrophobic surface property and the low water of crystallization content of magnesium stearate, which is also achieved through a subsequent drying step, which is preferably is performed after the application of the magnesium stearate coating, result in extremely low diffusion of water to the basic material of the implant body during subsequent shipping and storage of the implant. The local contamination present at the surface of the implant due to the production process as well as the precipitates at the surface due to the alloy composition of the implant body are embedded here in an inert form due to the magnesium stearate and therefore can no longer react under ambient conditions. Likewise, the release of particles with a low tendency to binding tendency from the surface of the implant body during dilatation can be prevented. These particles remain in the viscous magnesium stearate layer, which is highly flexible. This yields an increased hemocompatibility and/or biocompatibility.

Because of the magnesium stearate coating on the implant body, the coefficient of friction of the implant is lowered in an advantageous manner. As a result, lower forces may be applied in displacement of a stent as an implant in a catheter for example. Therefore, in the case of a stent, a more accurate fixation of the stent is made possible. Furthermore, crimping and the subsequent release of the implant at the site for treatment are simplified.

In a preferred exemplary embodiment of the inventive method, the magnesium stearate coating is applied by dipping in a solution containing magnesium stearate and a solvent, preferably acetone and/or isopropanol, and preferably at a temperature between approx. 10° C. and 40° C. Alternatively, the magnesium stearate layer may also be applied in such a way that said solution containing magnesium stearate is sprayed onto the body of the implant (spray coating). To do so, the part is suspended on a thin wire in a chamber and is sprayed on all sides by means of a rotating disk (batch holder).

In a preferred exemplary embodiment, the efficacy of the dipping process can be accomplished to by applying a pressure lower than the ambient pressure, preferably lower than approx. 90% of the ambient pressure, i.e. atmospheric pressure, at the site where the dipping process is performed. The resulting degassing effect leads to rapid filling of the filigree surface structure of the implant with magnesium stearate. After a retention time of a few minutes in the solution, preferably at least approx. 2 minutes, the implant body coated with magnesium stearate is removed from the immersion bath and is dried in a drying oven at a temperature above room temperature, preferably greater than approx. 30° C. It is especially preferable here if the drying temperature is as low as possible, i.e. between approx. 40° C. and approx. 70° C., because this leads to a slow release/evaporation of the at least one solvent, so that a pore-free first layer containing magnesium stearate is created.

The above statement of object is also achieved by an implant obtainable by an inventive method as described above. Such an implant has the advantages indicated above in conjunction with the inventive production process. The surface morphologies and surface compositions obtained due to the incorporation of hydrogen are characteristic of this treatment and are discernible on the finished manufactured implant.

Furthermore, the object as formulated above is achieved by an implant in which hydrogen is incorporated into at least a portion of the structure near the surface in a concentration of approx. 50 ppm to approx. 150 ppm. As explained above, a concentration of hydrogen in the concentration range indicated leads to especially effective acceleration of degradation.

In another exemplary embodiment, hydrogen is incorporated into the structure of a boundary layer of the implant body arranged near the surface, where the boundary layer has a thickness of max. approx. 15 µm. The stated thickness of the boundary layer with hydrogen is optimal with regard to the degradation behavior on the one hand and the risk of brittle fracture on the other hand.

It is also preferable that the implant has a roughened surface. An increased roughness of the surface of the implant body, which is advantageous for the application of an additional cover layer (e.g., magnesium stearate) or the degradation behavior, is achieved due to the hydrogen incorporation processes described above.

As already explained, it is also advantageous if the implant body has a phosphate in the boundary layer arranged near the surface. In this way, the biocompatibility of the implant is improved at least at the start of degradation in particular when using an iron alloy for the implant body.

It is also preferable if the surface of the implant body has at least partially a coating containing magnesium stearate and/or parylene and/or an active pharmaceutical substance. Preferred layer thicknesses of the parylene coating here are between approx. 0.5 µm and approx. 10 µm.

The preferred thickness of the magnesium stearate coating is approx. 0.5 µm to approx. 10 µm, preferably approx. 1.0 µm to approx. 5.0 µm. The concentration of the magnesium stearate in the additional coating is approx. between 80 wt % and 100 wt %.

Due to the incorporation of hydrogen into a boundary layer near the surface and the subsequent additional coating by means of magnesium stearate and/or parylene, the degradation time of the implant can be varied and adjusted within wide limits in a defined manner according to the respective intended purpose of the implant.

In a preferred exemplary embodiment, the body of the implant preferably contains a degradable metallic material, preferably predominantly iron, in particular more than 80 wt % iron, especially preferably at least 99 wt % iron, in particular in an alloy. Alternatively or additionally, manganese, zinc and/or tungsten may also be used as additional metallic materials. Since these implants can be manufactured inexpensively, they are especially popular for use for treatment of diseases of the human or animal body. In particular in the case of implants containing iron, the incorporation of hydrogen leads to a reduced degradation time. This closes a gap between the degradable and nondegradable alloys for implants.

EXAMPLES

The inventive method and/or the inventive implant is/are explained in the following examples. All the features described constitute the subject of the invention, regardless of how they are combined in the claims or their references back to preceding claims.

Example 1

An implant produced by laser cutting, deburring and electropolishing in the form of a stent consists of an iron-based alloy and is pickled for 10 minutes at room temperature in 30% HCl and then rinsed in distilled water. Depending on the alloy composition, the stent then losses mass in the amount of 3 to 8%. The roughness of the stent surface increases. An increase in the integral hydrogen content in a boundary layer from 15 ppm to 30 ppm is observed. The hydrogen can be detected in the carrier-gas hot-extraction method. The stated hydrogen concentration in the boundary layer is still not within the optimum concentration range given, but accelerated degradation is achieved already at the stated hydrogen concentration, in particular when the treated part of the boundary layer has an increased degree of conversion.

Example 2

A stent made of an iron-based alloy prepared by analogy with the first example is pickled for 10 minutes in a 20% $HNO_3$ solution at room temperature and then rinsed in distilled water. This is followed by a cathodic treatment in an alkaline phosphate solution containing at least one compound from the group of sodium phosphate, potassium phosphate, calcium dihydrogen phosphate, disodium phosphate, dipotassium phosphate and calcium hydrogen phosphate. Disodium phosphate, dipotassium phosphate and calcium hydrogen phosphate are less water-soluble here than the other compounds of the group.

For example, a stent is brought in contact with a stainless steel wire in an aqueous solution with 80 g/L $KH_2PO_4$ and is connected to the anode. The pH of the solution is approx. 9. At a bath voltage between 2 V and 8 V and a current density of 0.5 $A/dm^2$ to 1.5 $A/dm^2$, the stent surface is loaded with negatively charged phosphate ions over a period of 1 to 5 minutes at room temperature. These phosphate ions form a thin layer of sparingly water-soluble iron phosphates (Fe(II) or Fe(III) phosphates) on the surface of the stent. Likewise, the formation of iron diphosphate is also possible. The max. layer thickness is approx. 0.5 µm. It should be noted that no higher current density and no increase in treatment time are allowed, because otherwise the hydrogen content in the boundary layer would be minimized too much.

This surface, which now consists of Fe phosphates, has a higher biocompatibility than a pure iron surface. Furthermore, this surface provides temporary surface protection, which means that the iron stent does not corrode further during its storage time and therefore it is not necessary to shorten the minimum stability of the catheter. On the other hand, the iron phosphate surface is not corrosion-resistant enough to present a greater resistance to corrosive attack in the blood vessel. The surface containing iron phosphate thus functions as an inhibitor with an increased biocompatibility which acts temporarily (over the storage time).

Example 3

Like Example 2, but cathodic treatment of the implant is performed in an acidic solution containing phosphoric acid. For example, the phosphates listed in Example 2 are dissolved in the solution containing phosphoric acid.

The solution consists in particular of an aqueous 10-30% phosphoric acid in which the iron stent is brought in contact with a stainless steel wire and is connected as the anode as in Example 2 using the identical current and voltage parameters. The acid medium here produces further fissuring of the stent surface. Various iron phosphates are again formed.

Example 4

As in examples 1 to 3, with additional sealing of the rough surface of implant body with magnesium stearate or parylene C.

Coating with parylene C is performed from the gas phase. After a coating time of approx. one-half hour, a layer thickness of approx. 0.5 µm is achieved.

Alternatively, a magnesium stearate coating is applied to the implant surface. After performing one of Exemplary Embodiments 1 to 3 and then drying, the endoprosthesis is suspended from a plastic string (e.g., polyamide) and then immersed in the solution to apply the magnesium stearate. The solution consists of 9 parts high-purity acetone or isopropanol and 1 part magnesium stearate, for example. The immersion process takes place at room temperature in an evacuable desiccator in which a vacuum of approx. 100 mbar is created by means of a pump. In this way, the filigree microporous surface structures and/or undercuts and structures of a complex shape formed by the prior plasma-chemical pretreatment are effectively freed of residual gas. Complete coverage of the stent surface by the magnesium stearate in the solution may be accomplished in this way, such that it also penetrates into the surface structures and undercuts. After a retention time of approx. 3 minutes in the immersion bath, the desiccator is aerated, the implant is removed from the immersion body and then dried in a circulating air cabinet at a temperature of 60° C. while still suspended from the plastic string. The layer thickness of the magnesium stearate coating obtained in this way is in the range of approx. 0.5 to approx. 10 µm.

Due to the vacuum prevailing in the desiccator, the magnesium stearate is deposited very uniformly on the surface. A low drying temperature advantageously produces a slow release/evaporation of the solvent of the dipping solution, resulting in a pore-free magnesium stearate layer. If the implant produced in this way is a stent, then the body provided with the first layer and the intermediate layer may then be completed with a catheter and subjected to a radiation sterilization.

The magnesium stearate produces an additional sealing effect on the implant surface. This means that an implant treated in this way can either be stored for a longer period of time (e.g., until assembly of the catheter system) or may have a longer lifetime/functionality in the case of an orthopedic implant. This yields the possibility of maintaining mechanical stability for a longer period of time until resorption of the magnesium stearate. This leads to the possibility of use for an absorbable intramedullary nail in orthopedics, for example. Such a nail is resorbed by the osteoclasts of the spongiosa after a few months when its supporting effect is no longer needed. The magnesium stearate treatment also offers the advantage that the complex electropolishing of the implant (in particular in the case of stents) may be omitted or may be performed with much less effort.

As in the production of the parylene or magnesium stearate coating, the fissured surface of the implant may alternatively or additionally be coated with an active pharmaceutical substance. Preferred substances are indicated above in the description.

Detection of increased degradation of implants which are loaded with hydrogen can be performed by storage in PBS (phosphate buffered solution) or in SBF (simulated body fluid), for example. In the case of suitably treated stents with an implant body comprising an iron alloy with a composition of >50 wt % up to 99.99 wt % iron, with alloy elements such as Mn, Si, Pd, Pt, N, C, S and optionally additional alloy constituents, an increase in Fe elution up to a factor of 1.5 has been found after storage in SBF. Furthermore, due to the roughening effect, an increase in the size of the real surface area by a factor of 1.5 has been achieved after storage in PBS.

In the dimensioning of the inventive hydrogen loading of the implant body, the respective dimensions of the implant must also be taken into account. This will be demonstrated below on the basis of a stern as an example.

On the whole, the diameter of the internal structural area of a stent web loaded with an increased hydrogen content should amount to at least 50% of the total diameter of the stent web. Otherwise, there is the risk that the cracks emanating from the edge zone can no longer be stopped at the middle of the component. In this case, the respective stent can no longer perform its supporting function.

It may be estimated that at a thickness of the boundary layer with an increased hydrogen concentration of 5 µm, cracks run down to a depth of 10 µm into the matrix and the lifetime of the web of a stent 100 µm wide therefore drops to 80%. With a boundary layer thickness of 15 µm, the cracks are stopped by the structure of the stent body after approx. 25 µm. Thus, at a boundary layer thickness of 15 µm, the web cross section of a stent or of any other implant must amount to at least 170 µm×170 µm (=0.289 mm$^2$). The remaining crack-free cross-sectional area would then have edge lengths of 120 µm×120 µm (=0.144 mm$^2$) and would guarantee a degradation time within the desired time range.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A method for manufacturing an implant, in particular an intraluminal endoprosthesis, with a body containing metallic material, comprising the following steps:
    a) preparing the body of the implant, and
    b) incorporating hydrogen into at least a portion of the structure of the implant body near the surface,
    wherein the average concentration of hydrogen in the structural areas of the implant body where the incorporation takes place amounts to approximately 50 ppm to approximately 150 ppm after conclusion of the incorporation.

2. The method according to claim 1, characterized in that hydrogen is incorporated into the structure of a boundary layer of the implant body near the surface, where the boundary layer has a maximum thickness of approximately 15 µm.

3. The method according to claim 1, wherein to incorporate the hydrogen, at least a portion of the implant body is pickled by means of an acid and then is rinsed in distilled water.

4. A method for manufacturing an implant, in particular an intraluminal endoprosthesis, with a body containing metallic material, comprising the following steps:
    a) preparing the body of the implant, and
    b) incorporating hydrogen into at least a portion of the structure of the implant body near the surface,
    wherein to incorporate the hydrogen, at least a portion of the implant body is immersed in an acidic to basic electrolyte system and then is connected to the cathode of a voltage source, which is optionally acted upon with a current density of approximately 0.5 A/dm$^2$ to approximately 2 A/dm$^2$.

5. The method according to claim 4, wherein the electrolyte system contains at least one phosphate.

6. A method for manufacturing an implant, in particular an intraluminal endoprosthesis, with a body containing metallic material, comprising the following steps:
    a) preparing the body of the implant, and
    b) incorporating hydrogen into at least a portion of the structure of the implant body near the surface,
    wherein after the incorporation of the hydrogen, the implant body is coated with magnesium stearate and/or parylene and/or an active pharmaceutical substance on at least a portion of its surface.

* * * * *